United States Patent [19]

Acorn et al.

[11] Patent Number: 5,305,762
[45] Date of Patent: Apr. 26, 1994

[54] PATIENT VALVE INCORPORATING ONE-WAY CHECK VALVES FOR INFECTION CONTROL

[75] Inventors: Russell G. Acorn, White Bear Lake; Gary M. Hassebroek, Eagan, both of Minn.

[73] Assignee: Medical Graphics Corporation, St. Paul, Minn.

[21] Appl. No.: 948,041

[22] Filed: Sep. 21, 1992

[51] Int. Cl.$^5$ .................................................. A61B 5/08
[52] U.S. Cl. ................................. 128/716; 128/725; 128/730
[58] Field of Search .......... 128/716, 718–720, 128/725–726, 730, 200.11, 200.12, 200.13, 909, 911, 912, 914

[56] References Cited

U.S. PATENT DOCUMENTS

| | | | |
|---|---|---|---|
| 3,721,238 | 3/1973 | Wise et al. | 128/909 X |
| 4,416,273 | 11/1983 | Grimes | 128/912 X |
| 4,456,016 | 6/1984 | Nowacki et al. | 128/725 |
| 4,510,933 | 4/1985 | Wendt et al. | 128/912 X |
| 4,579,826 | 4/1986 | Bolton et al. | 128/730 X |
| 5,119,825 | 6/1992 | Huhn | 128/716 |

*Primary Examiner*—William E. Kamm
*Assistant Examiner*—Jeffrey R. Jastrzab
*Attorney, Agent, or Firm*—Haugen and Nikolai

[57] ABSTRACT

A single-use, disposable, elastomeric patient valve has a pair of one-way check valves disposed in the crosspiece portion thereof to create a barrier against patient infection. The check valves prevent contamination by a first patient of the reusable demand valve portion as he or she exhales into the patient valve and prevents the inhalation of possibly infected materials into the lungs, via the sampling chamber and associated tubing coupling same to the patient valve.

5 Claims, 1 Drawing Sheet

PATIENT VALVE INCORPORATING ONE-WAY CHECK VALVES FOR INFECTION CONTROL

BACKGROUND OF THE INVENTION

I. Field of the Invention

This invention relates generally to pulmonary performance testing equipment, and more particularly to an improved, disposable, single-use patient valve employed in the breathing circuit of such equipment.

II. Discussion of the Prior Art

In an earlier U.S. Pat. No. 5,119,825 to James Huhn and entitled "Multi-Functional Patient Valve", which is assigned to the assignee of the present application, there is described a single-use, disposable patient valve for use in cardiopulmonary test apparatus comprising a molded, flexible, elastomeric tubular body of a cruciform shape and cooperating with the stem portion of the cross are first and second selectively actuable clamps which, when actuated, pinch off the flow of gases across the pinched portions. The full teaching and description of the patient valve described in that aforereferenced patent are hereby incorporated by reference.

As is fully explained in U.S. Pat. No. 5,119,825, a procedure called lung diffusion is used in accessing a patient's lung volume. In this procedure, the cruciform shape elastomeric patient valve has a patient mouthpiece having a flow measuring capability connected to one end of its stem and the opposite end is open to the ambient. A gas demand valve is coupled to a first end of the patient valve's cross member while the opposite end of this cross member is coupled to a gas sample apparatus. In use, a first clamp is actuated for pinching the patient valve to block off ambient air and, during the patient's inspiratory phase, a test gas, such as a mixture of carbon monoxide and neon, is inhaled through the demand valve, through the multi-functional patient valve, and through the mouthpiece into the patient's lungs. Now, a second clamp is actuated pinching off the patient valve between the mouthpiece and the valve's cross member such that the patient is made to hold the inhaled gas sample within the lungs for a predetermined time interval. Following this time interval, the second clamping means is released while the first is maintained. The patient may now exhale, with the expired gases passing through the patient valve into the sample chamber. The first clamping means is then released allowing the patient to breathe ambient air. The collected gas sample can be analyzed to determine the capacity of the lungs to absorb oxygen.

Those skilled in the art can appreciate that during use, and especially during the expiratory phase of the testing cycle, the demand valve and the coupling hoses leading to the sample chamber are exposed to the patient's respiratory gases, including moisture particles entrained in the expired gas stream. While the patient valve itself is a single-use, disposable item, it is intended that the demand valve and the coupling equipment utilized to join the patient valve to the sample chamber are intended to be reusable. Noting that bacteria and other infectious germs or viruses may be resident in the moisture particles exhaled by one patient, it is imperative that a means be provided for maintaining isolation of the demand valve circuit from exhaled breath and the mouthpiece from exposure to flow from the sample chamber during inhalation so that a subsequent patient undergoing similar testing will not be exposed to bacteria and germs from a prior patient.

It is accordingly a principal object of the present invention to provide an improved single-use, disposable patient valve of the type described in the aforereferenced Huhn patent, with a means for isolating the demand valve circuit from a given patient's expiratory gases and that patient from the flow of air or other gases from the sampling circuit when inhaling to thereby inhibit the possibility of a infection by a subsequent patient using the equipment, albeit with a new patient valve installed.

SUMMARY OF THE INVENTION

The foregoing object and advantage of the invention is achieved in accordance herewith by providing a pair of one-way check valves in the cross-arm members of the cruciform elastomeric patient valve, the check valves being polarized so that during an inspiratory phase of the test, the gas sample equipment is effectively isolated from the patient valve while the test gas is permitted to flow through the demand valve into the patient's lungs, via the patient valve and mouthpiece member coupled to it. During the expiratory phase of the test cycle, the check valves operate to permit the expired gas to flow through the path leading to the sample chamber while blocking any flow back to the demand valve circuit. The two check valves introduced into the single-use, disposable patient valve are themselves of a sufficiently low-cost construction that it does not substantially increase the cost of the disposable patient valve to the point where economics would demand sterilization and reuse. Also those check valves do not materially increase the resistance to flow of inspired and expired gases through the mouthpiece. The demand valves incorporated into the disposable patient valve each comprise a rigid annular ring having a gas impervious flap affixed to a side surface thereof at a single hinge point, the flap being of a size to completely overlay the central aperture of the support ring. The outer dimension of the support ring is such that it may be firmly held in position within the cross arms of the elastomeric patient valve so as to be transverse to the direction of flow of gases through the cross arm. Because the gas impervious flaps on the check valves are only secured to their associated support ring at a single point, only a very small pressure differential across the valve is required to actuate the check valve from a gas blocking to a gas passing disposition.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
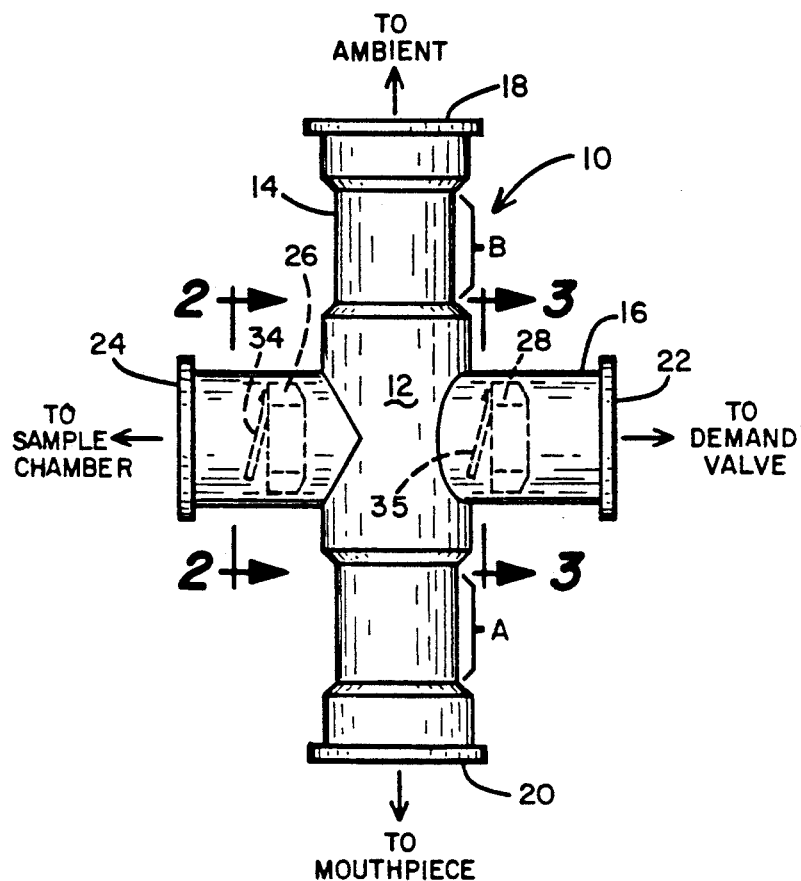
FIG. 1 is a top plan view of the multi-functional patient valve incorporating the present invention.

Referring first to FIG. 1, there is indicated generally by numeral 10 a single-use, disposable patient valve constructed in accordance with the present invention for use in cardiopulmonary test apparatus. It comprises a tubular body 12 which is molded from a thermoplastic elastomer and is generally cruciform in its geometry. It includes a stem portion 14 and a cross-piece portion 16 intersecting at generally right angles. As is fully explained in the aforereferenced Huhn patent, the wall thickness of the tubular cross-piece portion 16 is uniform, but the wall thickness of the stem portion 14 is of a reduced thickness in the zones identified by the brackets labeled A and B. It is these portions that cooperate with a clamping mechanism in which the patient valve 10 is placed so that the stem portion may be pinched closed in those zones during use of the patient valve.

With continued reference to FIG. 1, the upper end 18 of the stem portion 14 is open to the ambient while the lower end 20 of the stem portion is arranged to receive a tubular mouthpiece member therein. The right end 22 of the cross-piece portion of the cruciform patient valve 10 is designed to receive the stem portion of a demand valve therein. The left end 24 of the cross-piece portion 16 is coupled through suitable tubing to a sample chamber.

Figure 2:
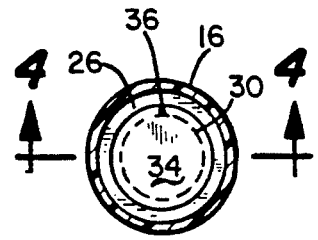
FIG. 2 is a cross-sectional view taken along the line 2—2 in FIG. 1.
Figure 3:
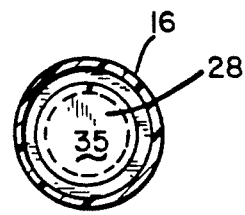
FIG. 3 is a cross-sectional view taken along the line 3—3 in FIG. 1.
Figure 4:
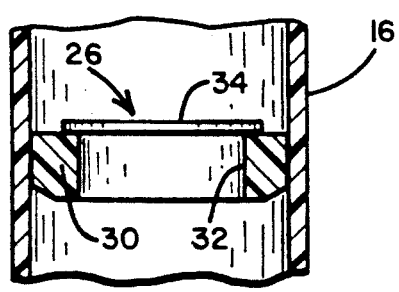
FIG. 4 is an enlarged sectional view taken along the line 4—4 in FIG. 2.
Figure 5:
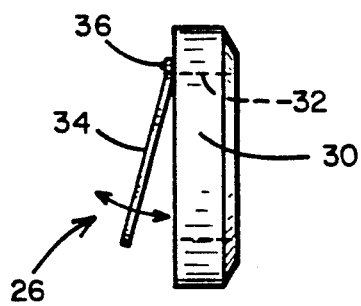
FIG. 5 is a side view of one of the check valves used in the multi-functional patient valve of FIG. 1.

The patient valve 10 of FIG. 1 is substantially identical to the patient valve described in the Huhn U.S. Pat. No. 5,119,825 except that in accordance with the present invention, first and second one-way check valves 26 and 28 are disposed in the cross-piece portion 16. The check valves each comprise an annulus 30 whose outside diameter is slightly larger than the unstretched diameter of the elastomer tubular portion 16 in which it resides. Hence, to place the check valve within the cross-piece portion of the patient valve, it is necessary to slightly stretch the elastomeric material which insures a secure gas-tight seal between the outer diameter of the annulus 30 and the wall of the tube 16. The annulus 30 has a central opening 32 extending through its thickness dimension and overlaying this opening is a gas impervious flap 34. The flap 34 has an outer diameter which is greater than the diameter of the opening 32 is anchored to the annulus 30 at a single point, as at 36 in FIG. 2.

The flap 34 is preferably formed from an elastomeric film, such as a polystyrene material, having a thickness in the range from about 0.003 inch to 0.008 inch and the attachment between it and the annulus 30 at point 36 is preferably achieved using a sonic spot weld.

As can be seen from FIG. 1, the one-way check valves 26 and 28 are positioned within the cross piece member 16 so that the flaps 34 and 35 open relative to the opening 32 in the annulus 30 by swinging to the left when viewed in FIG. 1.

Consider the operation of the improved patient valve during the course of a lung diffusion test. Initially, the patient is asked to breathe normally through the mouthpiece connected to the end 20 of the stem 14. At this time, the clamping means (not shown) associated with the zones A and B of the patient valve are deactivated and, thus, the patient breathes air from the ambient through the end 18 of the patient valve. Next, the clamp associated with zone B is operated to pinch that zone closed. Now, rather than breathing air when inhaling, the patient will be made to draw a carbon monoxide containing mixture from a gas supply (not shown) through the demand valve. Because of the negative pressure created by the patient's lungs, the flap 35 of the check valve 28 will open, allowing the carbon monoxide to flow through it and through the mouthpiece into the patient's lungs. At this time, however, the same negative pressure created by inhalation will cause the flap 34 of the check valve 26 to be drawn against the side wall surface of the annulus 30. Closure of the flap 34 thus blocks entrance of any back flow from the sampling chamber circuit coupled to the end 24 of the patient valve into a patient's lungs.

After inhaling the carbon monoxide, the second clamping means will be actuated to pinch closed the elastomeric material comprising zone A of the patient valve, thus forcing the patient to hold his or her breath for a predetermined length of time during which the inhaled carbon monoxide diffuses through the lung tissue into the blood. Following the termination of the predetermined delay, only the clamping means associated with zone A is released, opening up the path through the valve body in zone A and allowing the patient to exhale through the one-way check valve 26 into the sampling chamber. The clamping means associated with zone B is then reopened, again allowing the patient to breathe ambient air. As the patient exhales, the flap 34 associated with the one-way check valve 26 is forced opened by the pressure differential while that same pressure differential forces the flap 35 of the one-way check valve 28 to assume its gas-blocking relationship relative to the annulus 28 on which it is mounted. The exhaled gases are prevented from reaching the demand valve which is coupled to the right end 22 of the patient valve, thus preventing it from being contaminated by body fluids entrained in the expired gas mixture from the patient's lungs.

The check valves 26 and 28 are used strictly for infection control and not for gas flow control. The check valves themselves offer a very low resistance to flow because of the fact that the flexible flap members 34 and 35 thereof are fastened to their associated support rings at a single pin-point location. It has been found that a pressure differential of less than one centimeter of water across the valve is sufficient to open or close it, as the case may be, while still allowing up to 360 liters-per-minute of gas flow through the patient valve during its use.

It can be seen, then, that the improved patient valve of the present invention retains all of the functional and performance characteristics of the patient valve described in the aforereferenced Huhn Patent, the teachings of which have been incorporated by reference herein, while adding to it a means for preventing contamination of subsequent patients whose pulmonary performance is to be tested. That is to say, the one-way check valve's function to prevent the possible contamination of the demand valve by one patient so that a subsequent patient using the equipment will not be infected upon inhaling a gas through that demand valve. Likewise, because the one-way check valve associated with the sample chamber side of the patient valve closes during inhalation, had the tubing leading to the sample chamber been contaminated by a previous patient, the current patient would not draw a gas mixture into his or her lungs from the sample chamber when inhaling through the mouthpiece member.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. In patient valve for pulmonary test equipment of the type including a unitary hollow elastomeric body, said body including first, second, third and fourth tubular sections, each having an inner lumen, one end of each tubular section being joined and sealed in a common area to the other three tubular sections to allow fluid flow from any tubular section to any other tubular section without escaping from said body, said first and second tubular sections including zones in which said body is sufficiently elastic to close when squeezed and reopen when released, said first tubular section having its other end open to the ambient, said second tubular section adapted to be coupled to a patient mouthpiece, said third tubular section adapted to be coupled to a gas demand value and said fourth tubular section adapted to be coupled to a gas sampling chamber, the improvement comprising:

infection control valve means disposed in said third and fourth tubular sections for allowing gas flow from said demand vale through said patient mouthpiece and blocking gas flow from said gas sampling chamber when the patient inhales through said mouthpiece and for permitting gas flow from said mouthpiece to said gas sampling chamber while blocking gas flow from said mouthpiece to said demand valve when the patient exhales through said mouthpiece.

2. The apparatus as in claim 1 wherein said infection control valve means disposed in said third and fourth tubular sections comprise one-way check valves.

3. The apparatus as in claim 2 wherein each of said check valves comprises a rigid ring having an outer dimension corresponding to the size of said inner lumen of a respective one of said third and fourth tubular sections and a central opening; and a felxible flap member adhered to said rigid ring at a spot location, said flap member being of a size and shape to completely overlay said central opening.

4. The apparatus as in claim 3 wherein said flexible flap member comprises a gas impervious material.

5. The apparatus as in claim 4 wherein said gas impervious material is an elastomeric material having a thickness in the range from about 0.003 to 0.008 inch.

* * * * *

UNITED STATES PATENT AND TRADEMARK OFFICE
CERTIFICATE OF CORRECTION

PATENT NO. : 5 305 762
DATED : April 26, 1994
INVENTOR(S) : Russell G. Acorn, et al.

It is certified that error appears in the above-indentified patent and that said Letters Patent is hereby corrected as shown below:

Column 6, line 3, change "vale" to -- valve --.

Column 6, line 19, change "felxible" to -- flexible --.

Signed and Sealed this

Twenty-third Day of August, 1994

Attest:

BRUCE LEHMAN

Attesting Officer

Commissioner of Patents and Trademarks